United States Patent
Garcia Miralles et al.

(10) Patent No.: US 12,146,030 B2
(45) Date of Patent: Nov. 19, 2024

(54) METHOD FOR PRODUCING NON-ISOCYANATE POLYURETHANES

(71) Applicant: Henkel AG & Co. KGaA, Duesseldorf (DE)

(72) Inventors: Jose Garcia Miralles, Duesseldorf (DE); Maryluz Moreno Rueda, Tarragona (ES); Zeynep Beyazkilic, Tarragona (ES); Raquel Gavara Castell, Nules (ES); Xavier Elias Pera, Terrassa (ES)

(73) Assignee: Henkel AG & Co. KGaA, Duesseldorf (DE)

( * ) Notice: Subject to any disclaimer, the term of this patent is extended or adjusted under 35 U.S.C. 154(b) by 693 days.

(21) Appl. No.: 17/362,110

(22) Filed: Jun. 29, 2021

(65) Prior Publication Data

US 2021/0324141 A1 Oct. 21, 2021

Related U.S. Application Data

(63) Continuation of application No. PCT/EP2019/084398, filed on Dec. 10, 2019.

(30) Foreign Application Priority Data

Jan. 4, 2019 (EP) .................................. 19382006

(51) Int. Cl.
| | |
|---|---|
| C08G 71/04 | (2006.01) |
| C07D 209/42 | (2006.01) |
| C07D 235/30 | (2006.01) |
| C07D 295/135 | (2006.01) |

(52) U.S. Cl.
CPC .......... C08G 71/04 (2013.01); C07D 209/42 (2013.01); C07D 235/30 (2013.01); C07D 295/135 (2013.01)

(58) Field of Classification Search
None
See application file for complete search history.

(56) References Cited

U.S. PATENT DOCUMENTS

| | | | |
|---|---|---|---|
| 3,072,613 A | 1/1963 | Whelan, Jr. et al. | |
| 5,132,458 A | 7/1992 | Hoenel et al. | |
| 5,548,041 A | 8/1996 | Yamato et al. | |
| 5,786,402 A | 7/1998 | Bruchmann et al. | |
| 5,977,262 A | 11/1999 | Anderson | |
| 8,118,968 B2 | 2/2012 | Moeller et al. | |
| 9,260,564 B2 | 2/2016 | Lombardo et al. | |
| 9,309,218 B2 | 4/2016 | Woelfle et al. | |
| 10,577,463 B2 | 3/2020 | Zhao et al. | |
| 2007/0151666 A1 | 7/2007 | Moeller et al. | |
| 2008/0262096 A1 | 10/2008 | Mederski et al. | |
| 2014/0378648 A1 | 12/2014 | Soules et al. | |
| 2016/0326132 A1 | 11/2016 | Cramail et al. | |

FOREIGN PATENT DOCUMENTS

| | | |
|---|---|---|
| CN | 106795268 A | 5/2017 |
| EP | 1070733 A1 | 1/2001 |
| EP | 3098219 A1 | 11/2016 |
| EP | 3401350 A1 | 11/2018 |
| ES | 2127430 T3 | 4/1999 |
| JP | 2006009001 A | 1/2006 |
| JP | 2008526790 A | 7/2008 |
| JP | 2015502374 A | 1/2015 |
| JP | 2015229714 A | 12/2015 |
| WO | 2010081670 A2 | 7/2010 |
| WO | 2013092011 A1 | 6/2013 |

OTHER PUBLICATIONS

Sylvain Koeller et al., (Thio)Amidoindoles and (Thio)Amidobenzimidazoles: An Investigation of Their Hydrogen-Bonding and Organocatalytic Properties in the Ring-Opening Polymerization of Lactide, Chem. Eur. J. 2010, 16, pp. 4196-4205.
STN Registry, Columbus Ohio.
Zhao Yuhua et al., Thermal and mechanical properties of soy-based nonisocyanate polyurethane composites, Institute of Coal Chemistry Chinese Academy of Sciences, Taiyuan 030001, China, pp. 88-96, (2007).
Liu et al., Squaramide and amine binary H-bond organocatalysis in polymerizations of cyclic carbonates, lactones, and lactides, Polym. Chem., Aug. 2017, pp. 7054-7068.
Lombardo et al., Cooperative Catalysis of Cyclic Carbonate Ring Opening: Application Towards Non-Isocyanate Polyurethane Materials, Eur. J. Org. Chem. 2015, pp. 2791-2795.
Blain et al., Urea- and Thiourea-Catalyzed Aminolysis of Carbonates, ChemSusChem Sep. 2016, pp. 1-5.
International Search Report for International PCT Patent Application No. PCT/EP2019/084398 dated Feb. 20, 2020.

*Primary Examiner* — David J Buttner
(74) *Attorney, Agent, or Firm* — Sun Hee Lehmann

(57) ABSTRACT

The present application is directed to a method for producing non-isocyanate polyurethanes. More particularly, the application is directed to method for producing non-isocyanate polyurethanes by using a single catalyst component selected from an amidoindole derivative, a benzimidazole derivative and a squaramide derivative.

8 Claims, No Drawings

METHOD FOR PRODUCING NON-ISOCYANATE POLYURETHANES

FIELD OF THE INVENTION

The present application is directed to a method for producing non-isocyanate polyurethanes. More particularly, the application is directed to method for producing non-isocyanate polyurethanes by using a single catalyst component.

BACKGROUND TO THE INVENTION

The aminolysis of cyclocarbonates allows the preparation of non-isocyanate polyurethanes (NIPUs) that are toxic-reagent-free analogues of polyurethanes (PUs). The ring opening reactions of cyclic carbonates by primary and secondary amines at room temperature are too slow to be used at industrial scale, since they can take several days. For that reason, it is very important to develop improved catalyst system to accelerate the formation of non-isocyanate-based polyurethane which includes the activation of the monomers through the action of a catalyst. Efforts have been made to develop such catalyst for the aminolysis of cyclocarbonates with amines at room temperature.

ChemSusChem 2016, 9, 1-5 discloses a screening of catalytic systems based on urea derivatives and compares their behaviour with that exhibited by their thiourea analogues in the ring opening of propylene carbonate with cyclohexylamine. The pKa of the (thio)urea and unequal substitution pattern are critical for the efficiency of the carbonate opening. More acidic or more basic (thio)ureas afforded lower conversions. Actually, the cyclohexylamine is capable of deprotonating the most acidic (thio)urea derivatives [pKa(cyclohexylamine)=11.5 at 25° C.]. Consequently, the deprotonated catalyst is not able to activate the carbonate. Conversely, the less acidic catalysts do not activate the carbonyl strongly enough to allow nucleophilic attack of the amine.

US 2016/9260564 B2 discloses a cooperative catalyst system that includes a Lewis acid and a Lewis base for the ring opening of cyclic carbonates by primary amines at room temperature. The Lewis acid (LiOTf) and Lewis base (TBD and DBU) may work together to activate the electrophile (the carbonate) and the nucleophile (the amine). However, some of the catalysts have safety and health concerns (DBU) or are air-sensitivity (TBD and DBU). Moreover, a high quantity of each catalyst (more than 10%) is used to carry out the reactions.

US 2016/0326132 A1 teaches a method for preparing a poly(hydroxyurethane) using a step polymerization of 5-membered cyclic biscarbonates derived from renewable vegetable oils and primary polyamine, optionally in the presence of a catalyst such as a strong base and/or a nucleophile. As strong bases, Schreiner thiourea catalyst, the guanidine MTBD (7-methyl-1.5.7-triazabicyclo-[4.4.0]dec-5-ene), the amidine base DBU (1,8-diazabicyclo[5.4.0]undec-7-ene) and the guanidine TBD (1.5.7-triazabicyclo-[4.4.0]dec-5-ene) are used. The nucleophiles employed include DMAP (4-dimethylaminopyridine), the salt LiCl and ZnAc (zinc acetate). Moreover, a co-catalyst may be added. However, the reaction was carried out at a temperature range comprised between 60° C. and 105° C. that would be considered quite high for some industrial applications.

WO 2013/092011 A1 teaches a method for synthesis and use of 2-oxo-1,3-dioxolane-4-carboxamides in the preparation of polyhydroxyurethanes, polyhydroxycarbonates and hydroxysulfanylformates. The curing experiments using IPDA (isophorone diamine) and TMD (hexamethylenediamine isomeric mixture). However, the reaction using these new ester activated cyclocarbonates take long times (from 3 to 7 days) at room temperature.

WO 2013060950 A1 discloses a process for the preparation of a compound comprising a β-hydroxy urethane unit or a hydroxy-γ-pattern urethane. The reaction between a reactive cyclocarbonate with an amino reactive unit (—NH2) in the presence of a catalyst system is reported. The catalyst system includes an organometallic complex as the catalyst and a co-catalyst selected from the group of Lewis bases or tetra-alkyl ammonium salts. Nevertheless, both catalyst and co-catalyst are considered hazard and toxic.

EP 1070733 A1 describes a reaction of poly-functional oligomers containing epoxy and cyclocarbonate groups with aliphatic or cycloaliphatic amines. In the other hand, the reaction is carried out under nitrogen atmosphere and moreover, different ranges of temperature are used (80 to 120° C.), as well as some organic solvents.

US 2007151666 A1 describes a bonding agent system comprising two components to be used as adhesive/sealant. Cyclic carbonate groups and their mixture are reported as Component A and primary and secondary amines as component B. However, for the synthesis of the bonding agent used ethyl acetate as a solvent. Moreover, the cyclic carbonates were obtained using hazardous isocyanates.

Polym. Chem. 2017, 8, 7054 discloses the use of squaramides (hydrogen bonding donor) and amine co-catalysts as a versatile approach for ring opening polymerization of the three major types of cyclic ester monomers: lactides, cyclic carbonates, and lactones.

Chem. Eur. J. 2010, 16, 4196-4205 describes a mechanism of the ring opening polymerization of lactide catalyzed by two partner hydrogen-bonding organocatalysts. Certain am idoindoles, thio-amidoindoles, amidobenzimidazoles and thioamidobenzimidazoles are used as activators of the monomer. Furthermore, a co-catalyst, tertiary amine, which activates the growing polymer chain through hydrogen-bonding was also used.

Therefore, there is still a need to develop an improved method of producing a non-isocyanate based polyurethane by using a catalyst system which is not complicated and non-toxic for the ring opening reaction of a cyclic carbonate with an amine. In addition, the catalyst system is required to allow the ring opening reaction to be performed under room temperature so that the method of producing the non-isocyanate based polyurethane is suitable for industrial scale.

BRIEF DESCRIPTION OF THE INVENTION

In accordance with a first aspect of the present invention, there is provided a method for producing non-isocyanate-based polyurethane, said method comprising:

(1) providing a cyclic carbonate component, (2) providing an amine component selected from the group consisting of a primary amine, a secondary amine, and combination thereof, and (3) providing a single catalyst component that performs the ring opening reaction of the cyclic carbonate component with the amine component, selected from the group consisting of:

(a) an amidoindole derivative represented by Formula (I),

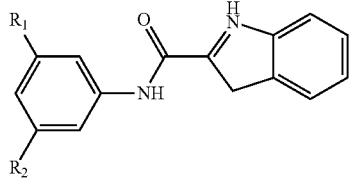

(I)

wherein $R_1$ and $R_2$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, (b) a benzimidazole derivative represented by Formula (II),

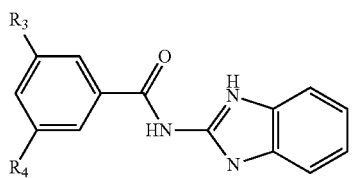

(II)

wherein $R_3$ and $R_4$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, and, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, (c) a squaramide derivative represented by Formula (III),

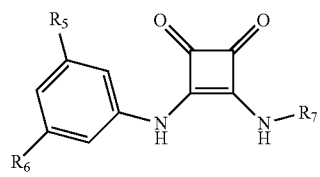

(III)

wherein
$R_5$ and $R_6$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, and $R_7$ represents a cyclo-$C_3$-$C_6$ alkyl group, a phenyl, a naphthyl, or a 5-10 membered heteroaryl consisting of carbon atoms and 1-3 heteroatoms selected from N, O, and S, optionally substituted by a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, or a cyclo-$C_3$-$C_6$ alkyl group, a phenyl, a naphthyl, or a 5-10 membered heteroaryl consisting of carbon atoms and 1-3 heteroatoms selected from N, O, and S.

Another aspect of the present invention is a single catalyst component according to the present invention for forming a non-isocyanate based polyurethane polymer using a cyclic carbonate component and an amine component.

Yet another aspect of the present invention is a non-isocyanate based polyurethane polymer, comprising a urethane linkage that is the reaction product of a cyclic carbonate component and an amine component formed in the presence of a single catalyst component according to the present invention.

DETAILED DESCRIPTION OF THE INVENTION

Definitions

As used herein, the singular forms "a", "an" and "the" include plural referents unless the context clearly dictates otherwise.

The terms "comprising", "comprises" and "comprised of" as used herein are synonymous with "including", "includes", "containing" or "contains", and are inclusive or open-ended and do not exclude additional, non-recited members, elements or method steps.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

The terms "preferred", "preferably", "desirably", "in particular" and "particularly" are used frequently herein to refer to embodiments of the disclosure that may afford particular benefits, under certain circumstances. However, the recitation of one or more preferable or preferred embodiments does not imply that other embodiments are not useful and is not intended to exclude those other embodiments from the scope of the disclosure.

The molecular weights given in the present text refer to weight average molecular weights (Mw), unless otherwise stipulated. All molecular weight data refer to values obtained by gel permeation chromatography (GPC), unless otherwise stipulated.

Unless otherwise stated, the amine values given were obtained by titration with 0.1 N hydrochloric acid—in accordance with ASTM D2572-91—and thereafter calculated back to mg KOH/g.

As used herein, room temperature is 23° C. plus or minus 2° C.

As used herein, the term "aromatic group" means a mono- or polynuclear aromatic hydrocarbon group.

As used herein, "alkyl group" refers to a monovalent group that is a radical of an alkane and includes straight-chain and branched organic groups, which groups may be substituted or unsubstituted.

Specifically, as used herein, "$C_1$-$C_6$ alkyl" group refers to an alkyl group that contains 1 to 6 carbon atoms. Examples of alkyl groups include, but are not limited to: methyl; ethyl; propyl; isopropyl; n-butyl; isobutyl; sec-butyl; tert-butyl; n-pentyl; and, n-hexyl. In the present invention, such alkyl groups may be unsubstituted or may be substituted with one or more substituents such as halo, nitro, cyano, amido, amino, sulfonyl, sulfinyl, sulfanyl, sulfoxy, urea, thiourea, sulfamoyl, sulfamide and hydroxy. The halogenated derivatives of the exemplary hydrocarbon radicals listed above might, in particular, be mentioned as examples of suitable substituted alkyl groups. In general, however, a preference for unsubstituted alkyl groups containing from 1-6 carbon atoms ($C_1$-$C_6$ alkyl)—for example unsubstituted alkyl groups containing from 1 to 4 carbon atoms ($C_1$-$C_4$ alkyl) or 1 or 2 carbon atoms ($C_1$-$C_2$ alkyl)—should be noted.

As used herein, "$C_1$-$C_6$ alkylene" means a divalent linear or branched, saturated hydrocarbon radical having from 1 to 6 carbon atoms, which radical may be substituted or unsubstituted. For completeness, suitable substituents are those mentioned herein above in the definition of alkyl groups. And non-limiting examples thereof include methylene, ethylene, trimethylene, propylene, tetramethylene and pentamethylene.

It is noted that the term "polyisocyanate" is intended to encompass pre-polymers formed by the partial reaction of the aforementioned aliphatic, cycloaliphatic, aromatic and heterocyclic isocyanates with polyols to give isocyanate functional oligomers, which oligomers may be used alone or in combination with free isocyanate(s).

As used herein, the term "catalytic amount" means a sub-stoichiometric amount of catalyst relative to a reactant.

The term "essentially free" is intended to mean herein that the applicable group, compound, mixture or component constitutes less than 0.1 wt. %, based on the weight of the defined composition.

The non-isocyanate-based polyurethane of the present invention is produced by the ring opening reaction of a cyclic carbonate component with an amine component under the presence of a single catalyst component as described below. This statement does not preclude the presence of further reactants in the ring opening reaction except additional catalyst.

Generally, a single catalyst component that performs the ring opening reaction of the cyclic carbonate component with the amine component is selected from the group consisting of an amidoindole derivative, a benzimidazole derivative and a squaramide derivative. The inventors have surprisingly found that a single catalyst component can achieve an excellent yield of non-isocyanate-based polyurethane.

According to the present invention, the amidoindole derivatives are represented by Formula (I) as below:

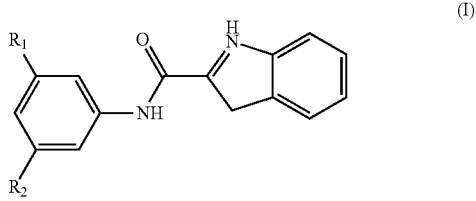

wherein $R_1$ and $R_2$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl group, or a sulfamoyl group. Preferably, $R_1$ and $R_2$ each independently represents a hydrogen, a halogen, a $C_1$-$C_6$ alkyl group, a $C_1$-$C_6$ alkoxy group, a halo-$C_1$-$C_6$ alkyl group, or an arylsulfonyl group. More preferably, $R_1$ represents a halogen, a $C_1$-$C_6$ alkyl group, a $C_1$-$C_6$ alkoxy group, a halo-$C_1$-$C_6$ alkyl group, or an arylsulfonyl group, and $R_2$ represents a hydrogen.

In one embodiment, $R_1$ is a halogen, such as fluorine, chlorine and bromine, and $R_2$ is hydrogen in Formula (I).

In another embodiment, $R_1$ is a halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl, and $R_2$ is hydrogen in Formula (I).

In yet another embodiment, $R_1$ is a $C_1$-$C_6$ alkoxy group, such as methoxy, ethoxy, propoxy, isopropoxy and butoxy, and $R_2$ is hydrogen in Formula (I).

In yet another embodiment, $R_1$ and $R_2$ each independently represents an arylsulfonyl group, such as benzenesulfonyl, or hydrogen in Formula (I).

According to the present invention, the benzimidazole derivative is represented by Formula (II) as below,

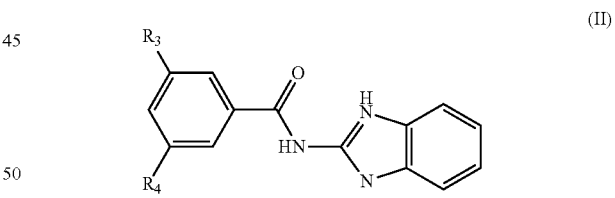

wherein $R_3$ and $R_4$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group. Preferably, $R_3$ and $R_4$ each independently represents a hydrogen, a halogen, a $C_1$-$C_6$ alkyl group, a $C_1$-$C_6$ alkoxy group, a halo-$C_1$-$C_6$ alkyl group, or an arylsulfonyl group. More preferably, $R_3$ represents a halogen, a $C_1$-$C_6$ alkyl group, a $C_1$-$C_6$ alkoxy group, a halo-$C_1$-$C_6$ alkyl group, or an arylsulfonyl group, and $R_4$ represents a hydrogen.

In one embodiment, $R_3$ is a halogen, such as fluorine, chlorine and bromine, and $R_4$ is hydrogen in Formula (II).

In another embodiment, $R_3$ is a halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl, and $R_4$ is hydrogen in Formula (II).

In yet another embodiment, $R_3$ is a $C_1$-$C_6$ alkoxy group, such as methoxy, ethoxy, propoxy, isopropoxy and butoxy, and $R_4$ is hydrogen in Formula (II).

In yet another embodiment, $R_3$ and $R_4$ each independently represents an arylsulfonyl group, such as benzenesulfonyl, or hydrogen in Formula (II).

According to the present invention, the squaramide derivative is represented by Formula (III),

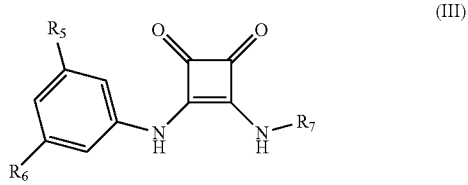

wherein
$R_5$ and $R_6$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, and
$R_7$ represents a cyclo-$C_3$-$C_6$ alkyl group, a phenyl, a naphthyl, or a 5-10 membered heteroaryl consisting of carbon atoms and 1-3 heteroatoms selected from N, O, and S, optionally substituted by a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, a phenyl, a naphthyl, or a 5-10 membered heteroaryl consisting of carbon atoms and 1-3 heteroatoms selected from N, O, and S.

Preferably, $R_5$ and $R_6$ each independently represents a hydrogen, a halogen, a $C_1$-$C_6$ alkyl group, a halo-$C_1$-$C_6$ alkyl group, a $C_1$-$C_6$ alkoxy group, a halo-$C_1$-$C_6$ alkoxy group, or a $C_1$-$C_6$-alkylsulfonyl group, and $R_7$ represents a cyclo-$C_3$-$C_6$ alkyl group, a phenyl, or a 5-10 membered heteroaryl consisting of carbon atoms and 1-3 heteroatoms selected from N, O, and S, optionally substituted by a halogen, a $C_1$-$C_6$ alkyl group, a halo-$C_1$-$C_6$ alkyl group, a cyclo-$C_3$-$C_6$ alkyl group, a $C_1$-$C_6$ alkoxy group, a halo-$C_1$-$C_6$ alkoxy group, or a cyclo-$C_3$-$C_6$ alkyl group, a phenyl, a naphthyl, or a 5-10 membered heteroaryl consisting of carbon atoms and 1-3 heteroatoms selected from N, O, and S.

In one embodiment, $R_5$ is a halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl, $R_6$ is hydrogen, and $R_7$ is a cyclo-$C_3$-$C_6$ alkyl group substituted by a 5-10 membered heteroaryl consisting of carbon atoms and 1-3 heteroatoms selected from N, O, and S, such as (1-piperidinyl)cyclohexyl in Formula (III).

In another embodiment, $R_5$ and $R_6$ both are halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl, and $R_7$ is a phenyl group substituted by a halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl in Formula (III).

In yet another embodiment, $R_5$ and $R_6$ both are halo-$C_1$-$C_6$ alkyl group, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, and dichloropropyl, and $R_7$ is a cyclo-$C_3$-$C_6$ alkyl group, such as cyclohexyl in Formula (III).

In yet another embodiment, $R_5$ and $R_6$ both are hydrogen, and $R_7$ is a phenyl group in Formula (III).

In yet another embodiment, $R_5$ and $R_6$ each independently represents an arylsulfonyl group, such as benzenesulfonyl, or hydrogen, and $R_7$ is a cyclo-$C_3$-$C_6$ alkyl group, a phenyl, or a 5-10 membered heteroaryl consisting of carbon atoms and 1-3 heteroatoms selected from N, O, and S in Formula (III).

Examples of catalyst suitable to be used as the single catalyst component in the present invention are compounds as follows:

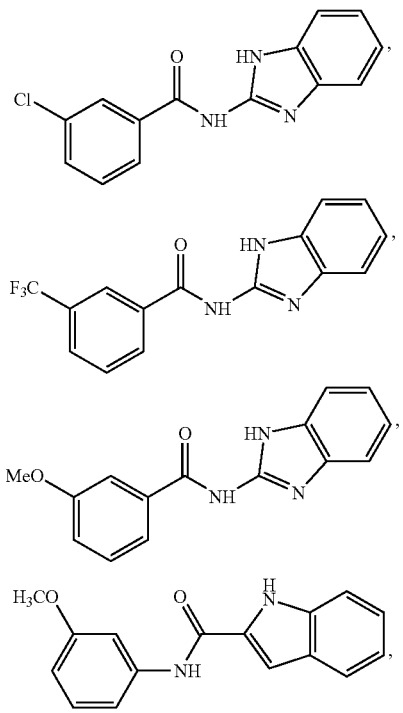

-continued

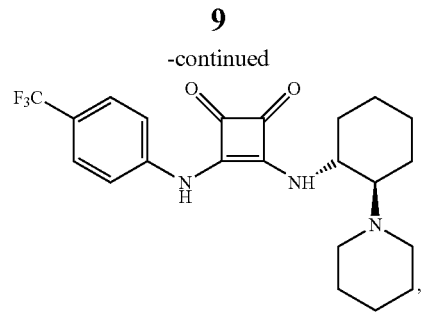

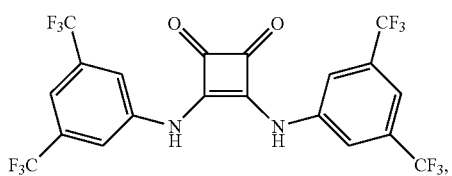, and

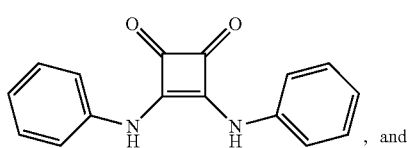

Preferably, the single catalyst component is selected from the compounds as below:

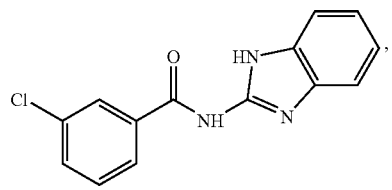,

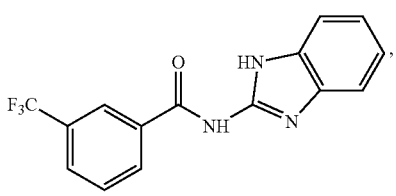,

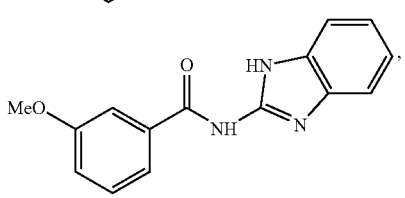,

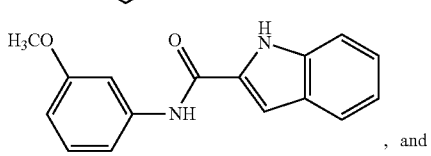, and

-continued

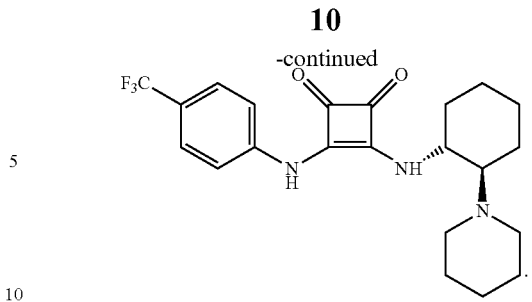

Whilst the determination of an appropriate catalytic amount of a compound is facile to a person of ordinary skill in the art, it is preferred that the single catalyst component is present in an amount of from 1 to 15 mol %, preferably from 5 to 10 mol %, based on the number of moles of the cyclic carbonate component.

The catalysts may be available from commercial source for example Sigma-Aldrich or prepared according to the following citations: Chemistry—A European Journal 2010, 16, 14, 4196-4205, J. Med. Chem., 1997, 40 (8), pp 1201-1210 and J. Am. Chem. Soc. 1947, 69, 2459-2461.

In the first step of the method for producing non-isocyanate-based polyurethane according to the present invention, a cyclic carbonate component is provided.

Although there is no limitation to the cyclic carbonates to be used as the component in the method, a five membered cyclic carbonate is preferred. The five membered cyclic carbonate can be represented by Formula (IV) or (V)

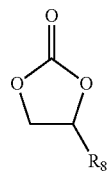

(IV)

wherein $R_8$ represents a $C_1$-$C_6$ alkyl group, a halo-$C_1$-$C_6$ alkyl group, a hydroxy-$C_1$-$C_6$ alkyl group, a $C_2$-$C_6$ alkenyl group, a $C_1$-$C_6$ alkoxy group, a halo-$C_1$-$C_6$ alkoxy group, an ether groups, a polyether group, an ester group, a polyester group, an amide group, a polyamide group, a urethane group, a polyurethane group, a urea group, a polyurea group, an acetal groups, or a polyacetal group, and preferably, $R_8$ represents a $C_1$-$C_6$ alkyl group such as methyl, ethyl, propyl, butyl, an ester group such as methyl formate group, methyl acetate group, methyl propionate group, ethyl formate group, or an amide group, for example N—$C_1$-$C_6$ alkylamide group, such as N-methylamide, N-ethylamide, N-propylamide, or N-butylamide,

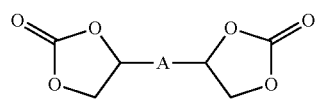

(V)

wherein A an organic group, which contains at least one functional group selected from an ether group, a polyether group, an ester group, a polyester group, an amide group, a polyamide group, a urethane group, a polyurethane group, a urea group, a polyurea group, an acetal group, and a polyacetal group, and preferably is an organic group contains ether group, such as ethylene glycol monobutyl ether group, ethylene glycol monophenyl ether group, diethylene glycol monomethyl ether group, diethylene glycol monobutyl ether group, diethylene glycol dimethyl ether group, diethylene glycol methylethyl ether group, diethylene glycol diethyl ether group, triethylglycol, triethylene glycol monomethyl ether group, triethylene glycol monoethyl ether group, propylene glycol monomethyl ether group, propylene glycol monoethyl ether group, propylene glycol monobutyl ether group, dipropylene glycol monomethyl ether group, dipropylene glycol monoethyl ether group, tripropylene glycol monomethyl ether, butylene glycol monomethyl ether, butylene glycol monomethyl ether, or hexylene glycol monomethyl ether, and/or an ester group.

According to the present invention, the cyclic carbonate can be activated or non-activated. The non-activated carbonates have an electron-releasing group such as $C_1$-$C_6$ alkyl group alkyl group at $R_8$ group position in Formula (I). Such non-activated cyclic carbonates exhibit a slow polymerization rate towards amines. The activated carbonates refer to those having a heteroatom, such as N, O, or S at $R_8$ group position (β position) and preferably close to the ring structure, which may improve/activate its reactivity towards amines.

Surprisingly, the inventors have found that by using the single catalyst component in the method for producing non-isocyanate-based polyurethane according to the present invention, the ring opening reaction of the activated carbonates, and even the non-activated carbonates with amines can perform under a lower reaction temperature (5° to 50° C. such as room temperature) with a higher conversion rate (at least 40%) in a shorter reactive times (within 24 hours).

Examples of the cyclic carbonate suitable to be used as component in the present invention are compounds as follows:

In the second step of the method for producing non-isocyanate-based polyurethane according to the present invention, an amine component is provided. The amine component to be used in the present invention can be selected from the group consisting of a primary amine, a secondary amine, and combination thereof. Preferably, the amine component is selected from the group consisting of 1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine, N-methylcyclohexylamine, N,N'-diisopropylethylenediamine, N,N'-diethylenediamine, N-methyl-1,3-propanediamine, N-methylethylenediamine, N,N,N',N'-tetramethyl-1,2-diaminoethane, N,N,N',N'-tetramethyl-1,4-diaminobutane, N,N,N',N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine, norborylamine and mixture thereof. More preferably, the amine component is selected from the group consisting of butylamine, dibutylamine, methylcyclohexylamine, and mixture thereof.

In step (c), the ring opening reaction of cyclic carbonate component with the amine component is performed with the assistance of the single catalyst component according to the present invention.

In step (c), the weight ratio of the cyclic carbonate component and the amine component is set as 2:1 to 1:2, and preferably 1:1 to 1:1.5. The single catalyst component is present in an amount of from 1 to 15 mol %, preferably from 5 to 10 mol %, based on the number of moles of the cyclic carbonate component.

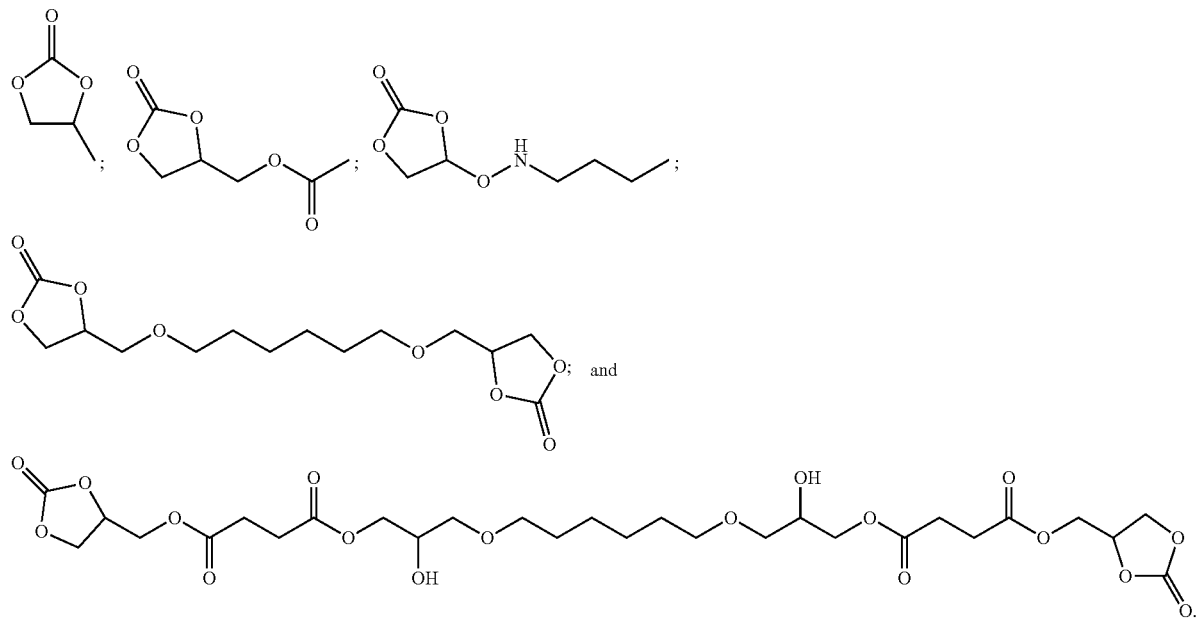

The cyclic carbonates may be available from commercial source for example Sigma-Aldrich or prepared according to the following citations: US 2014/0378648 A1, WO 2013/92011, EP 3098219 B1, or EP 3401350 A1.

Although not wishing to be bound to a particular theory, it is believed that the ring opening reaction is performed due to specific intermolecular interactions between the hydrogen-bonding single catalyst component and cyclic carbonate as a hydrogen-bond acceptor.

Surprisingly, the inventors have found that the single catalyst component according to the present application can efficiently facilitate a fast ring opening reaction by activating the cyclic carbonate by hydrogen-bonding effect at room temperature, and thus is suitable for the application in industrial scale. The single catalyst component intentionally contains no any other catalytic component such as catalyst or co-catalyst, unless avoidable impurities. The hydrogen-bonding effect of the squaramide derivative with a five membered cyclic carbonate can be illustrated as follows:

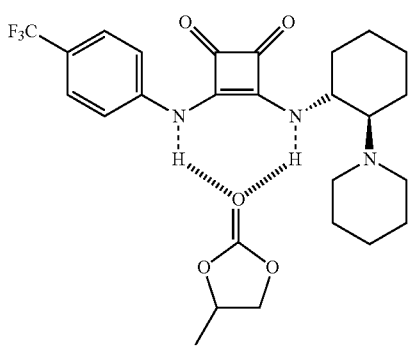

Whilst the optimum operating temperature for this stage of the process may be determined by the skilled artisan through experimentation, a suitable temperature range of from 0° to 80° C. may be mentioned, with a preferred temperature range being from 5° to 50° C., 20° C. to 35° C. or even room temperature.

The process pressure is not critical. As such, the reaction can be run at sub-atmospheric, atmospheric, or super-atmospheric pressures but pressures at or above atmospheric pressure are preferred.

Good results have been obtained where the ring opening reaction is performed under anhydrous conditions. In addition, the ring opening reaction can be carried out under air atmosphere, and the inert atmosphere is not a critical point according to the present invention.

The reaction can also be performed in solvent-free conditions or with solvent. If employed, suitable solvents should be inert: they should contain no functional groups that react with the starting compounds. Mention may thus be made of: halogenated hydrocarbons, illustratively methylene chloride, chloroform, perchloroethylene or 1,2 dichloroethane, aromatic hydrocarbons, illustratively toluene or benzene; aliphatic hydrocarbon solvents having from 5 to 12 carbon atoms, such as heptane, hexane or octane; ethers such as diethyl ether, methyl ethyl ether, diisopropyl ether, dioxane and tetrahydrofuran; and, esters such as ethyl acetate, amyl acetate and methyl formate. Of these solvents, halogenated hydrocarbons preferred.

The reaction time to obtain adequate conversion of reactant anhydride will be dependent on various factors such as temperature, catalyst type and type of cyclic carbonate. The reaction can be monitored by 1H NMR over time. Generally, the time which is sufficient for the reaction to take place will be from 2 to 36 hours, for instance from 4 to 8 hours or from 4 to 7 hours.

In one embodiment, the conversion of the cyclic carbonate reaches at least 40%, preferably at least 70%, and more preferably at least 80% over 24 hours. In one particular embodiment, the conversion of the non-activated cyclic carbonate reaches at least 40% over 24 hours. In another particular embodiment, the conversion of the activated cyclic carbonate reaches at least 40% over 5 hours. In yet another particular embodiment, the conversion of the activated cyclic carbonate reaches at least 70% over 24 hours.

In another aspect, the present invention is directed to a single catalyst component for forming a non-isocyanate based polyurethane polymer using a cyclic carbonate component and an amine component, and the single catalyst component is selected from the group consisting of an amidoindole derivative, a benzimidazole derivative and a squaramide derivative represented, as described above.

In yet another aspect, the present invention discloses a non-isocyanate based polyurethane polymer, comprising a urethane linkage that is the reaction product of a cyclic carbonate component and an amine component formed in the presence of the single catalyst component according to the present invention. The non-isocyanate based polyurethanes have a urethane linkage that is formed in the absence of isocyanate moieties, which linkages may be structurally similar to isocyanate base urethane linkages with the exception of an adjacent primary or secondary hydroxyl group.

Various features and embodiments of the disclosure are described in the following examples, which are intended to be representative and not limiting.

EXAMPLES

The following materials and abbreviations are employed in the Examples:
PC: Propylene carbonate from Sigma-Aldrich
CCA1: (2-oxo-1,3-dioxolan-4-yl)methyl acetate
CCA2: (2-oxo-1,3-dioxolan-4-yl)butylcarboxamide
CCA3: cyclic carbonate resin having formula

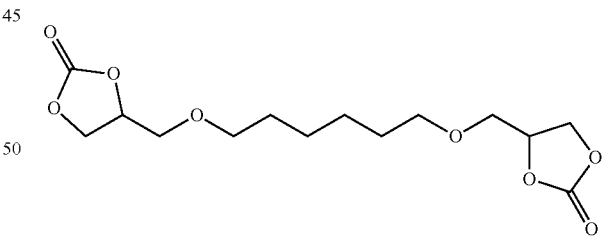

CCA4: cyclic carbonate resin having formula

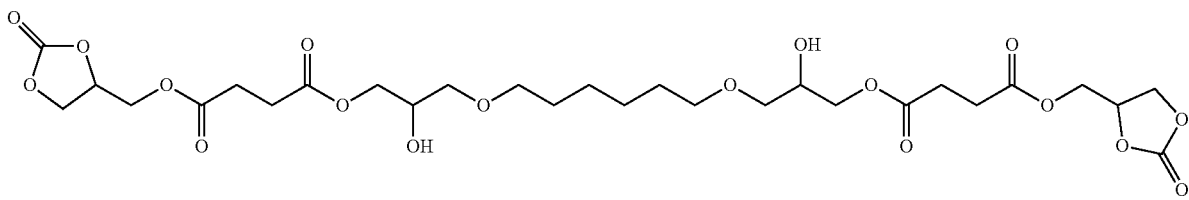 [SMILES: O=C(CCC(=O)OCC1COC(=O)O1)OCC(O)COCCCCCCOCC(O)COC(=O)CCC(=O)OCC1COC(=O)O1]

BA: n-butylamine from Sigma-Aldrich
DBA: di-n-butylamine from Sigma-Aldrich
MCA: methylcyclohexylamine from TCI
BCA: benzimidazole derivative from Sigma-Aldrich having formula

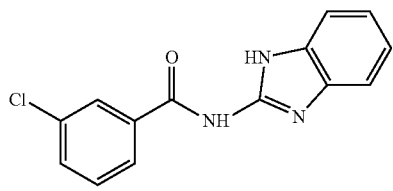 [SMILES: O=C(Nc1nc2ccccc2[nH]1)c1cccc(Cl)c1]

C3: amidoindole derivative having formula

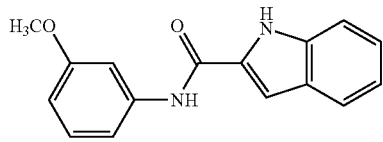 [SMILES: COc1cccc(NC(=O)c2cc3ccccc3[nH]2)c1]

C4: benzimidazole derivative having formula

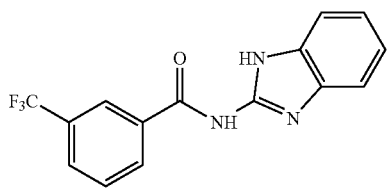 [SMILES: O=C(Nc1nc2ccccc2[nH]1)c1cccc(C(F)(F)F)c1]

C5: benzimidazole derivative having formula

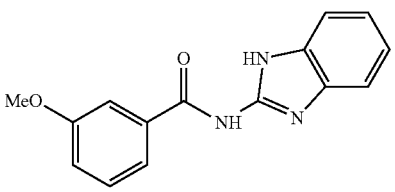 [SMILES: COc1cccc(C(=O)Nc2nc3ccccc3[nH]2)c1]

SQ: squaramide derivative from Sigma-Aldrich having formula

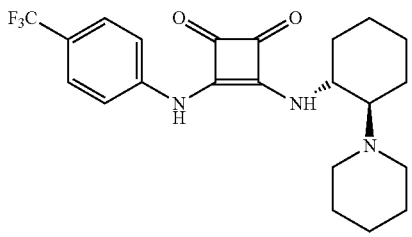

TBD: 1,5,7-triazabicyclo-[4.4.0]dec-5-ene from Sigma-Aldrich
Preparation of Cyclic Carbonate CCA1:
(2-oxo-1,3-dioxolan-4-yl)methyl acetate (CCA1) was prepared according to Example 2 of US 2014/0378648 A1.

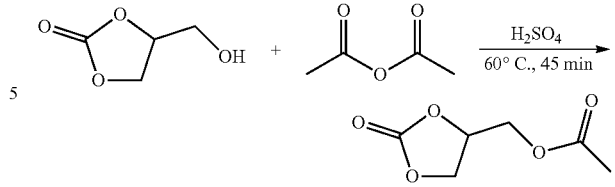

In a two-necked flask equipped with a condenser was introduced the glycerol carbonate (13.42 g, 0.11 mol) and acetic anhydride (11.17 g, 0.11 mol) and one drop of sulfuric acid. The reaction was stirred and heated at 60° C. in during 45 minutes in air. Then, the reaction was cooled at room temperature. After that the product was extracted with chloroform and washed ten times with distillated water and dried over anhydridous magnesium sulfate and rotaevaporated. The yield of reaction was 34%.

Preparation of Cyclic Carbonate CCA2:
(2-oxo-1,3-dioxolan-4-yl)butylcarboxamide (CCA2) was prepared according to JOC 2003, 68, 4999-5001, and Example 11 of WO 2013/92011.

In the first step, the carboxylic acid derivative was prepared from glycerol carbonate following a similar procedure reported on JOC 2003, 68, 4999-5001.

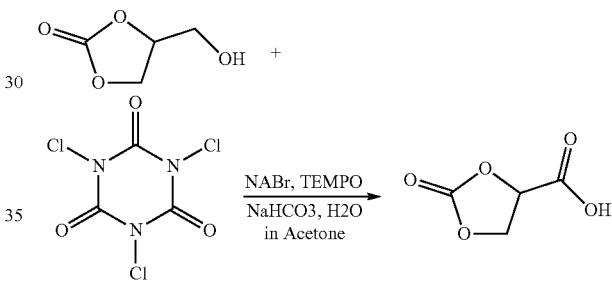

Glycerol carbonate (5.5 g, 0.042 mol) was dissolved in 65 mL of acetone and cooled at 0° C., then $H_2O$ (0.762 mL, 0.042 mol), NaBr (0.218 g, 0.002 mol) and TEMPO (0.066 g, 0.000423 mol) were successively added to the solution. Finally, trichloroisocyanuric acid (20.27 g, 0.084 mol) was slowly added during 10 minutes. The mixture was stirred during 18 h at room temperature. Then, the mixture was treated with 25 mL of isopropanol and filtered through a sintered glass Buchner funnel. The filtered liquid was concentrated under vacuum and the residue was treated with 50 mL of a saturated solution of $NaHCO_3$. The aqueous phase was washed with AcOEt (3×50 mL) and then acidified with 1M HCl up to pH ca. 1. The product was extracted with AcOEt (3×100 mL) and the organic phase was dried with $MgSO_4$. Finally the solvent was evaporated to yield 3.23 g of 2-oxo-1,3-dioxolane-4-carboxylic acid. The yield was 58%.

In the second step, (2-oxo-1,3-dioxolan-4-yl)butylcarboxamide (CCA2) was synthesized from carboxylic acid derivative prepared according to example 9 reported in Patent application WO 2013/092011 A1.

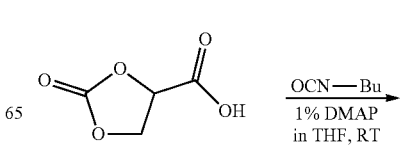

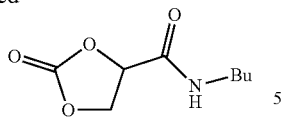

2-oxo-1,3-dioxolane-4-carboxylic acid (2.5 g, 0.019 mol) was dissolved in anhydrous THF (60 mL) under argon atmosphere. Then, n-butyl isocyanate (2.2 mL, 0.019 mol) and 4-dimethylaminopyridine (0.023 g, 0.00019 mol) were added. The solution was stirred at room temperature for 5 days. Then, silicon dioxide was added and the mixture was stirred for 45 min. After filtration, the solvent was evaporated and the crude was recrystallized from cyclohexane, giving 1.27 g of CCA2. The yield was 36%.

Preparation of Cyclic Carbonate Resin CCA3:

The cyclic carbonate resin having the following formula was prepared according to EP 3098219 B1.

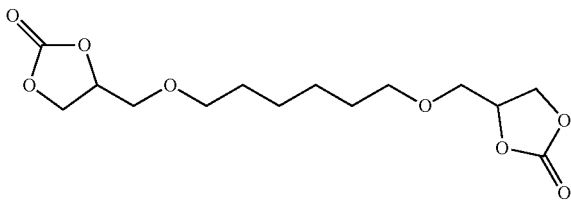 [SMILES: O=C1OCC(COCCCCCCOCC2COC(=O)O2)O1]

Preparation of Cyclic Carbonate Resin CCA4:

The cyclic carbonate resin having formula was prepared according to EP 3401350 A1.

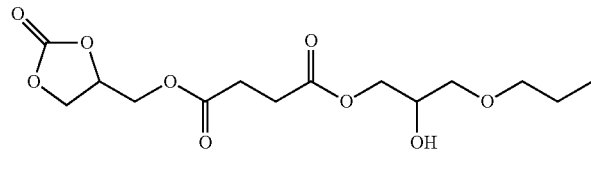

Preparation of Amidoindole Derivative C3:

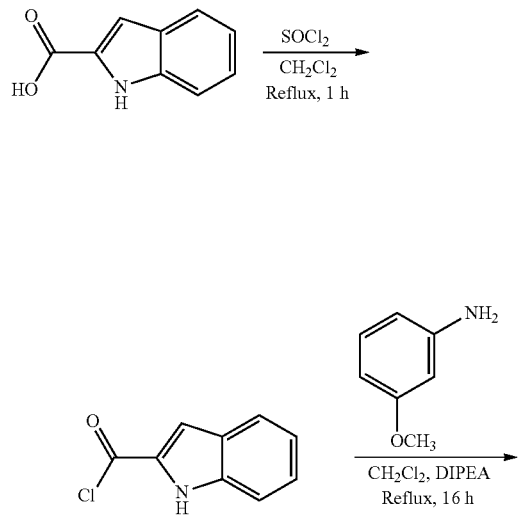

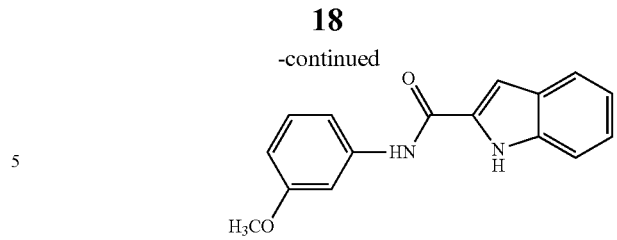

A solution of indole-2-carboxylic acid (0.483 g, 0.003 mol) and thionyl chloride (2.2 mL, 0.03 mol) in dried $CH_2Cl_2$ (10 mL) was heated at reflux for 2 h under argon and then evaporated. The residue was dried under vacuum for 30 min and dissolved in dried $CH_2Cl_2$ (10 mL) and a mixture of m-anisidine (0.308 g, 0.0025 mol) and N,N-diisopropylethylamine (0.517 g, 0.004 mol) in dried $CH_2Cl_2$ (5 mL) was added dropwise under argon atmosphere. The solution was stirred at room temperature for 20 min, and then heated at reflux for 16 hours. After cooling the mixture at room temperature, it was diluted with $CH_2Cl_2$ (30 mL) and then successively washed with saturated aqueous $NaHCO_3$ (3×10 mL), saturated aqueous $NH_4Cl$ (2×10 mL), water (2×10 mL) and brine (20 mL). Then the organic phase was dried over $MgSO_4$ and evaporated. The resulting crude was recrystallized in $CHCl_3$, giving C3 in 27% yield.

Preparation of Benzimidazole Derivative C4:

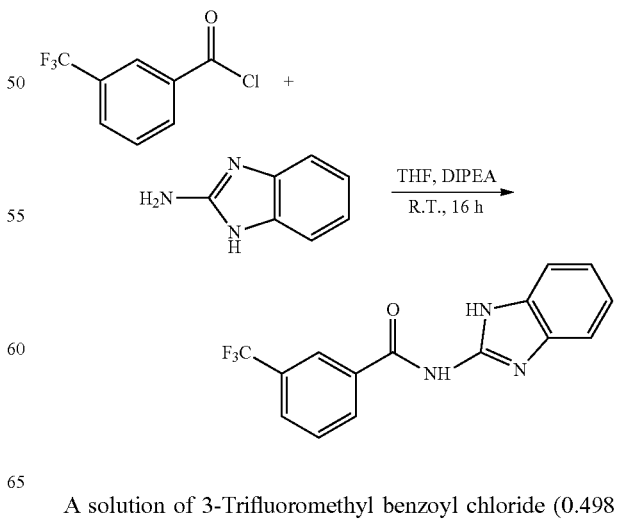

A solution of 3-Trifluoromethyl benzoyl chloride (0.498 mL, 0.0033 mol) in dried THF (5 mL) was added dropwise to a solution of 2-aminobenzimidazole (0.399 g, 0.003 mol) and N,N-diisopropylethylamine (0.99 mL, 0.0057 mol) in dried THF (15 mL). The mixture was stirred at room temperature for 16 h under argon atmosphere and evaporated. The residue was dissolved in $CH_2Cl_2$ (35 mL) and the solution was washed with saturated $NH_4Cl$ (2×30 ml), saturated aqueous $NaHCO_3$ (2×15 mL), water (2×15 mL) and brine (15 mL), dried over $Na_2SO_4$, and evaporated. The product precipitated in the aqueous phases with a yield of 25%.

Preparation of Benzimidazole Derivative C5:

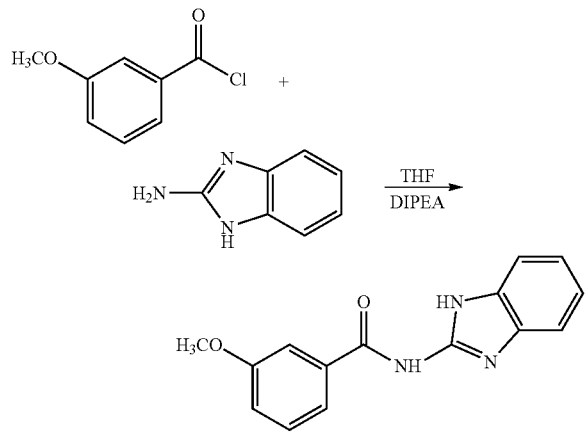

A solution of 3-methoxybenzoyl chloride (1.126 g, 0.0066 mol) in dried THF (10 mL) was added dropwise to a solution of 2-aminobenzimidazole (0.800 g, 0.006 mol) and N,N-diisopropylethylamine (2 mL, 0.0114 mol) in dried THF (30 mL). The mixture was stirred at room temperature for 16 h under argon atmosphere and evaporated. The residue was dissolved in $CH_2Cl_2$ (70 mL) and the solution was washed with saturated $NH_4Cl$ (2×30 mL), saturated aqueous $NaHCO_3$ (2×30 mL), water (2×30 mL) and brine (1×30 mL), dried over $Na_2SO_4$, and evaporated. Then the resulting sample was recrystallized in $CHCl_3$/MeOH.

Example 1: Reaction of PC and MCA by Using Catalysts or No Catalyst

Equimolar amounts of non-activated cyclic carbonate PC (0.102 g, 0.001 mol) and N-methylcyclohexamine (0.113 g, 0.001 mol) and 5 mol % of catalyst were mixed at room temperature and the reaction was followed by 1H-NMR. The results are summarized in Table 1.

TABLE 1

Kinetic studies of PC+ MCA system

| Time (hours) | No Catalyst | BCA | C4 | C5 | SQ | TBD |
|---|---|---|---|---|---|---|
| 0.0* | 0 | 1 | 2 | 1 | 0 | 8 |
| 3.0 | 0 | 14 | 14 | 19 | 9 | 10 |
| 5.0 | 3 | 24 | 24 | 27 | 15 | 12 |
| 24.0 | 16 | 54 | 49 | 45 | 40 | 24 |

*The zero time corresponds to the very first time such as 1 or 2 minutes after blending all the components.

As shown above, the effect of the catalysts BCA, C4, C5 and SQ was more remarkable at short times of reaction (5 hours) where the mentioned catalysts reached conversions from 10% to 20%. At the same 5 hours the reaction without catalyst was virtually unreactive. In addition, at longer times of reaction (1 day), BCA, C4, C5 and SQ helped to reach conversions around 40%.

Example 2: Reaction of Ether Type Cyclic Carbonate and BA in Solvent by Using Catalysts or No Catalyst CCA3 (0.116 g, 0.0003 mol) was dissolved in 0.5 mL of CDCl3. Then, 5 mol % of the catalyst were added and mixed until the blend was homogeneous (15-30 minutes). Then, BA (0.044 g, 0.0006 mol) was added to the mixture and stirred. The reactions were monitored by 1H-NMR. The reaction conversion was calculated respect to formation of product and consumption of the amine. The results are summarized in Table 2.

TABLE 2

Kinetic studies of ether type cyclocarbonate resin CCA3 + BA system in $CDCl_3$

| Time (hours) | No Catalyst | BCA | C3 | C4 | C5 | SQ | TBD |
|---|---|---|---|---|---|---|---|
| 0.0 | 6 | 20 | 2 | 16 | 5 | 6 | 4 |
| 3.0 | 17 | 49 | 39 | 55 | 37 | 58 | 35 |
| 5.0 | 28 | 61 | 47 | 61 | 57 | 64 | 44 |
| 24.0 | 62 | 78 | 71 | 79 | 78 | 77 | 71 |

As can be seen in Table 2, all the inventive catalysts increased the conversion after 3 and 5 hours of the reaction. Even at zero time using BCA and $C_4$ (benzimidazoles with electron-withdrawing groups) the conversion was higher than the conversion reached without catalyst. After 1 day of reaction, all the catalysts reached higher conversions. In contrast, TBD achieved a lower conversion. At that time, all the catalysts efficiently promoted the reaction between CCA3 and BA and reached higher conversions than the blank reaction.

Example 3: Reaction of Ether Type Cyclic Carbonate and BA without Solvent by Using Catalysts or No Catalyst The reactions between ether type cyclocarbonate resins and amines were carried out in bulk with or without catalyst. The amine BA (0.044 g, 0.0006 mol) were mixed with 5 mol % of catalyst until the blend was homogeneous (1-2 min). Then, resin CCA3 (0.116 g, 0.0003 mol) were added to the mixture and stirred. The reactions were monitored by $^1$H-NMR. The reaction conversion was calculated with respect to the formation of product and the consumption of amine, the results are summarized in Table 3.

TABLE 3

Kinetic studies of ether type cyclocarbonate resin CCA3 + BA without solvent

| Time (hours) | BCA | C3 | C4 | SQ | TBD |
|---|---|---|---|---|---|
| 0.0 | 58 | 51 | 65 | 62 | 53 |
| 1 | 76 | 80 | 83 | 81 | 77 |

TABLE 3-continued

Kinetic studies of ether type cyclocarbonate resin CCA3 + BA without solvent

| Time | Conversion (%) | | | | |
|---|---|---|---|---|---|
| (hours) | BCA | C3 | C4 | SQ | TBD |
| 3 | 84 | 88 | 85 | 87 | 82 |
| 5 | 87 | 87 | 89 | 86 | 84 |
| 24 | 93 | 90 | 92 | 90 | 88 |

Under these conditions of reaction, the catalytic effect was greatly observed in very short times, C4 and SQ were comparable to TDB without the disadvantages that the last one represents for the process and the final product. Moreover, BCA, C3 and C5 attained higher conversions than the non-catalyzed reaction. On the other hand, after one hour of reaction all the samples reached conversions around 80% including the blank reaction.

Example 4: Reaction of Ester Type Cyclic Carbonate Resin and BA with Solvent by Using Catalyst The reactions between ester type cyclocarbonate resins and amines were carried out using two different solvents such as ethyl acetate and chloroform. CCA4 (0.218 g, 0.0003 mol), 5 mol % of catalyst and 0.5 mL of ethyl acetate were placed into a vial and stirred until complete dispersion of the catalyst. Then, BA (0.044 g, 0.0006 mol) was added. The reactions were monitored by $^1$H-NMR. The reaction conversion was calculated respect to the formation of product, the results are summarized in Table 4.

TABLE 4

Kinetic studies of esther type cyclocarbonate CCA4 +BA in EtOAc.

| Time | Conversion (%) | | | | |
|---|---|---|---|---|---|
| (hours) | BCA | C3 | C4 | SQ | TBD |
| 0.0 | 37 | 26 | 32 | 20 | 16 |
| 3 | 87 | 80 | 76 | 76 | 60 |
| 5 | 92 | 82 | 94 | 85 | 79 |
| 24 | 92 | 90 | 96 | 87 | 79 |

As shown in Table 4, all catalysts attained higher conversions. On the other hand, after 5 hours of reaction all the samples reached conversions around 80%.

The invention claimed is:

1. A method for producing a non-isocyanate-based polyurethane, comprising:
   (1) providing a cyclic carbonate component,
   (2) providing an amine component selected from the group consisting of a primary amine, a secondary amine, and combination thereof, and
   (3) providing a single catalyst component that performs the ring opening reaction of the cyclic carbonate component with the amine component, selected from the group consisting of:

(a) an amidoindole derivative represented by Formula (I),

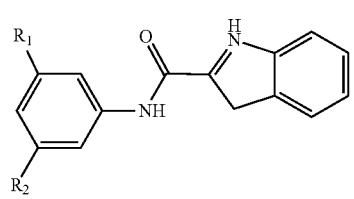

wherein $R_1$ and $R_2$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, (b) a benzimidazole derivative represented by Formula (II),

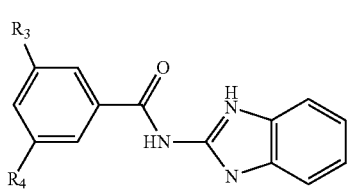

wherein $R_3$ and $R_4$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, and (c) a squaramide derivative represented by Formula (III),

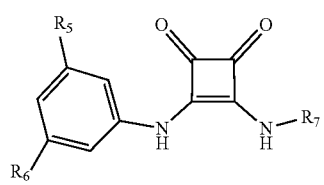

wherein $R_5$ and $R_6$ each independently represents a hydrogen, a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, an ester group, a carbonyl group, a $C_1$-$C_6$-alkoxycarbonyl group, an aryloxycarbonyl group, a $C_1$-$C_6$-alkylsulfinyl group, an arylsulfinyl group, a $C_1$-$C_6$-alkylsulfonyl group, an arylsulfonyl groups, or a sulfamoyl group, and $R_7$ represents a cyclo-$C_3$-$C_6$ alkyl group, a phenyl, a naphthyl, or a 5-10 membered heteroaryl consisting of carbon atoms and 1-3 heteroatoms selected from N, O, and S, optionally substituted by a halogen, a nitro group, a cyano group, a hydroxyl group, a $C_1$-$C_6$ alkyl group, a halo-$C_1$-$C_6$ alkyl group, a hydroxy-$C_1$-$C_6$ alkyl group, a cyclo-$C_3$-$C_6$ alkyl group, a $C_2$-$C_6$ alkenyl group, a $C_1$-$C_6$ alkoxy group, a halo-$C_1$-$C_6$ alkoxy group, a phenyl, a naphthyl, or a 5-10 membered heteroaryl consisting of carbon atoms and 1-3 heteroatoms selected from N, O, and S.

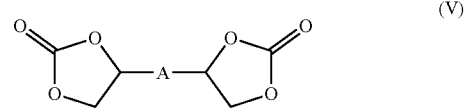

wherein A an organic group, which contains at least one functional group selected from an ether group, a polyether group, an ester group, a polyester group, an amide group, a polyamide group, a urethane group, a polyurethane group, a urea group, a polyurea group, an acetal group, and a polyacetal group.

3. The method according to claim 1, wherein the cyclic carbonate component is selected from at least one of the following compounds:

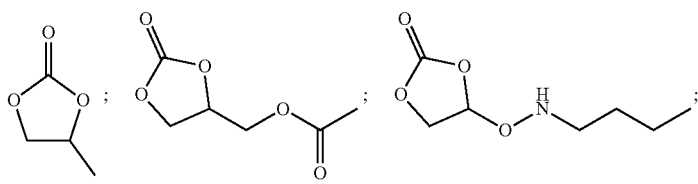

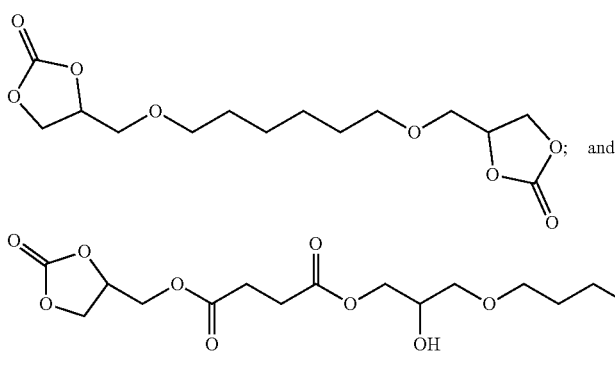

2. The method according to claim 1, wherein the cyclic carbonate component is a five membered cyclic carbonate represented by Formula (IV) or (V)

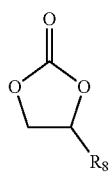

wherein $R_8$ represents a $C_1$-$C_6$ alkyl group, a halo-$C_1$-$C_6$ alkyl group, a hydroxy-$C_1$-$C_6$ alkyl group, a $C_2$-$C_6$ alkenyl group, a $C_1$-$C_6$ alkoxy group, a halo-$C_1$-$C_6$ alkoxy group, an ether groups, a polyether group, an ester group, a polyester group, an amide group, a polyamide group, a urethane group, a polyurethane group, a urea group, a polyurea group, an acetal groups, or a polyacetal group, 4. The method according to claim 1, wherein the amine is selected from mono- and dipropyl amine, mono- and dibutyl amine, mono- and dicyclohexylamine, ethylmethylamine, morpholine, methylcyclohexylamine, N,N-dialkylethylenediamines, N,N,N-trialkylethylenediamine, N,N'-dialkylpropanediamines, and N,N,N'-trialkylpentanediamine.

5. The method according to claim 1, wherein the single catalyst component is selected from the following compounds:

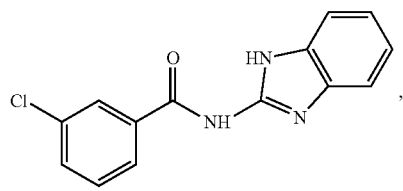

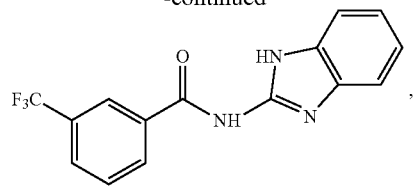,

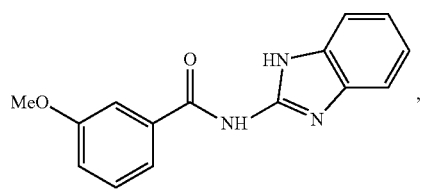,

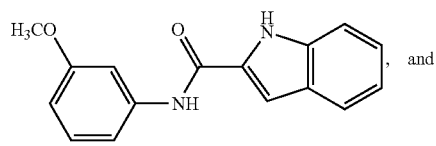, and

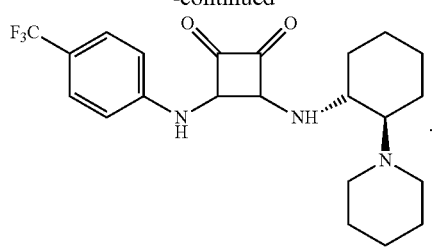.

6. The method according to claim 1, wherein the ring open reaction is performed under a temperature from 0° C. to 80° C.

7. The method according to claim 1, wherein the single catalyst component is present in an amount of from 1 to 15 mol %, based on the number of moles of the cyclic carbonate component, component.

8. The method according to claim 1, wherein the weight ratio of the cyclic carbonate component and the amine component is 2:1 to 1:2.

* * * * *